United States Patent
Pan et al.

(10) Patent No.: US 7,395,706 B2
(45) Date of Patent: *Jul. 8, 2008

(54) MICRO SAMPLE HEATING APPARATUS AND METHOD OF MAKING THE SAME

(75) Inventors: Chin-Chang Pan, Taipei Hsien (TW); Yu-Fu Kang, Taipei (TW)

(73) Assignee: Touch Micro-System Technology Inc., Yang-Mei, Taoyuan Hsien (TW)

( * ) Notice: Subject to any disclaimer, the term of this patent is extended or adjusted under 35 U.S.C. 154(b) by 33 days.

This patent is subject to a terminal disclaimer.

(21) Appl. No.: 11/426,015

(22) Filed: Jun. 23, 2006

(65) Prior Publication Data

US 2007/0234794 A1    Oct. 11, 2007

(30) Foreign Application Priority Data

Apr. 6, 2006    (TW) .............................. 95112127 A

(51) Int. Cl.
*G01F 1/68*    (2006.01)
(52) U.S. Cl. ................................... 73/204.26; 250/288
(58) Field of Classification Search .................. 73/204, 73/204.26; 250/288
See application file for complete search history.

*Primary Examiner*—Andre J Allen
(74) *Attorney, Agent, or Firm*—Winston Hsu

(57) ABSTRACT

A micro sample heating apparatus has a substrate, a micro heating device disposed on a first surface of the substrate, a cavity having an inclined sidewall and corresponding to the micro heating device positioned in a second surface of the substrate, and an isolation structure positioned on the second surface of the substrate. The isolation structure has an opening corresponding to the cavity, and the cavity and the opening form a sample room.

16 Claims, 7 Drawing Sheets

MICRO SAMPLE HEATING APPARATUS AND METHOD OF MAKING THE SAME

BACKGROUND OF THE INVENTION

1. Field of the Invention

The present invention relates to a micro sample heating apparatus and method of making the same, and more particularly, to an integrated micro sample heating apparatus that requires no additional package process and method of making the same.

2. Description of the Prior Art

A micro sample heating apparatus is common equipment in a laboratory. The micro sample heating apparatus is used to heat a sample (normally a liquid sample) to a required temperature for the convenience of successive analysis. Please refer to FIG. 1 through FIG. 3. FIG. 1 through FIG. 3 are schematic diagrams illustrating a conventional micro sample heating apparatus 10, wherein FIG. 1 depicts a heating unit 20, FIG. 2 depicts a sample room unit 30, and FIG. 3 illustrates the conventional micro sample heating apparatus 10 in use. As shown in FIG. 1 through FIG. 3, the conventional micro sample heating apparatus 10 is composed of a heating unit 20, and a sample room unit 30. The heating unit 20 includes a substrate 22, and a micro heating device 24 disposed on the substrate 22. The sample room unit 30, disposed on the micro heating device 24, includes a slide 32 and an isolation structure 34. The isolation structure 34 is a flexible circular spacer, and the central opening 36 of the isolation structure 34 and the slide 32 constitute a sample room.

The conventional micro sample heating apparatus 10, however, suffers from some disadvantages. First, the heating rate of the conventional micro sample heating apparatus 10 depends on the thickness of the slide 32. The thinner the slide 32 is, the fast the heating rate becomes. However, the thickness of the slide 32 is inversely proportional to the price of the slide 32, and a thinner slide 32 will increase the cost of the conventional micro sample heating apparatus 10. Also, the slide 32 with a thinner thickness is more fragile. In addition, the heating unit 20 and the sample room unit 30 are fabricated separately. In other words, the sample room unit 30 is not placed on the heating unit 20 until using the conventional micro sample heating apparatus 10. Therefore, the heating unit 20 and the sample room unit 30 of the conventional micro sample heating apparatus 10 are not effectively integrated, causing inconvenience in use.

SUMMARY OF THE INVENTION

It is therefore one object of the claimed invention to provide a micro sample heating apparatus and method of making the same to improve the heating efficiency and integration of micro sample heating apparatus.

According to the claimed invention, a micro sample heating apparatus is provided. The micro sample heating apparatus includes a substrate, a micro heating device disposed on a first surface of the substrate, a cavity having an inclined sidewall and corresponding to the micro heating device positioned in a second surface of the substrate; and an isolation structure positioned on the second surface of the substrate. The isolation structure has an opening corresponding to the cavity, and the cavity and the opening form a sample room.

According to the claimed invention, a method of fabricating micro sample heating apparatuses is provided. First, a substrate is provided, and a plurality of micro heating devices is formed on a first surface of the substrate. Then, a plurality of cavities corresponding to the micro heating devices are formed in a second surface of the substrate. Each cavity has an inclined sidewall. Subsequently, an isolation structure having a plurality of openings is provided, and the isolation structure is bonded to the second surface of the substrate. Each opening is corresponding to each cavity, and each cavity and each opening corresponding to the cavity form a sample room.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
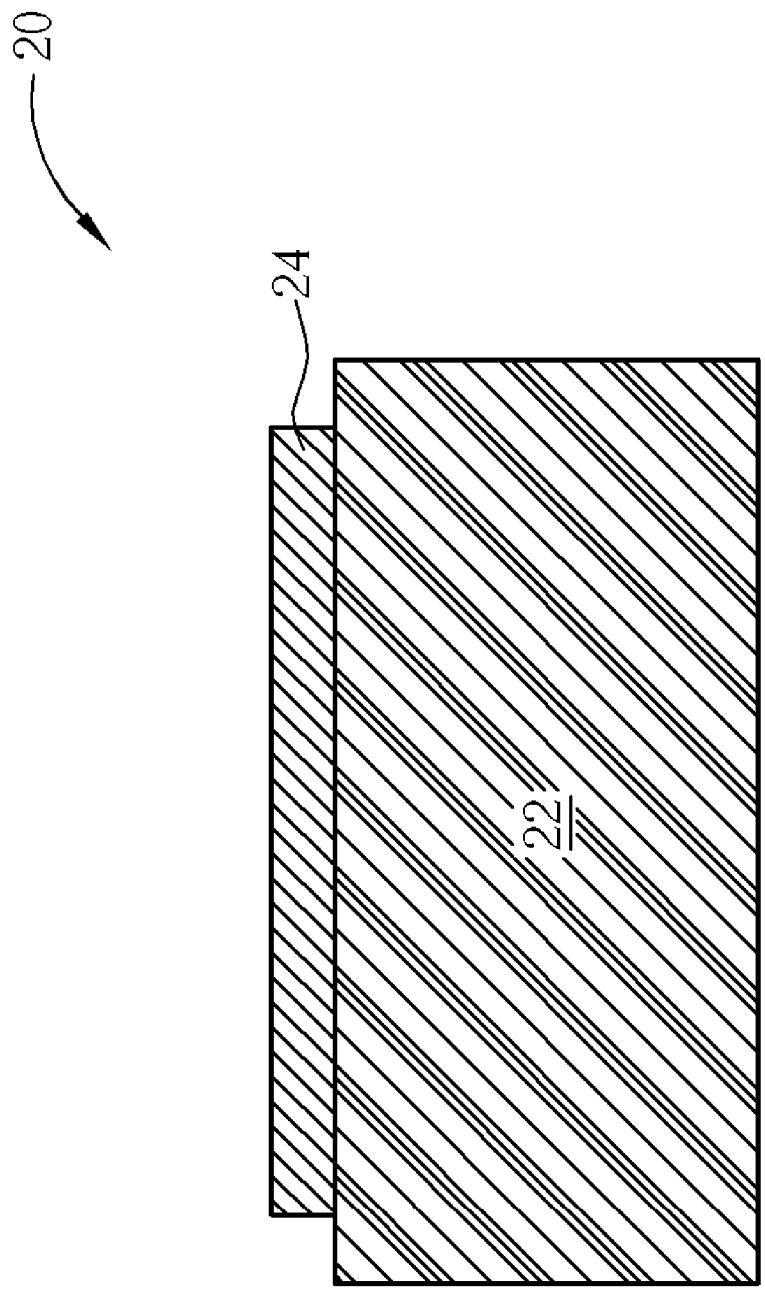
FIG. 1 through FIG. 3 are schematic diagrams illustrating a conventional micro sample heating apparatus.
Figure 2:
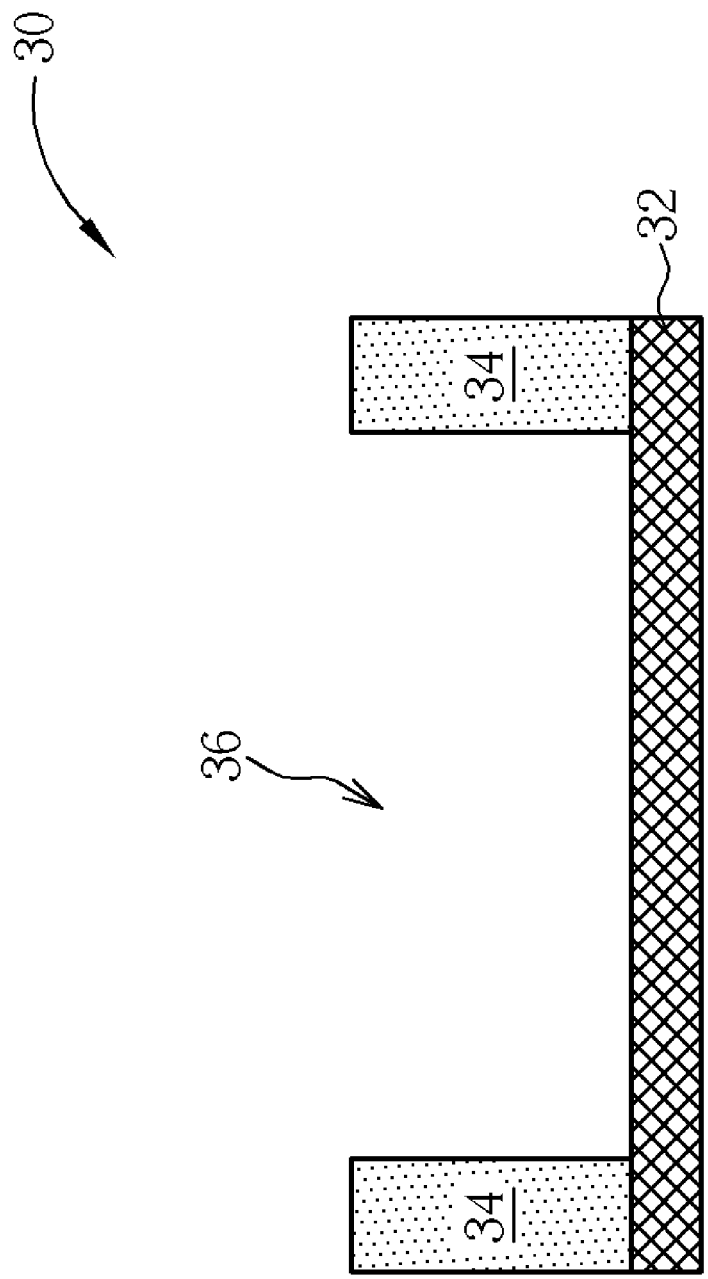
Figure 3:
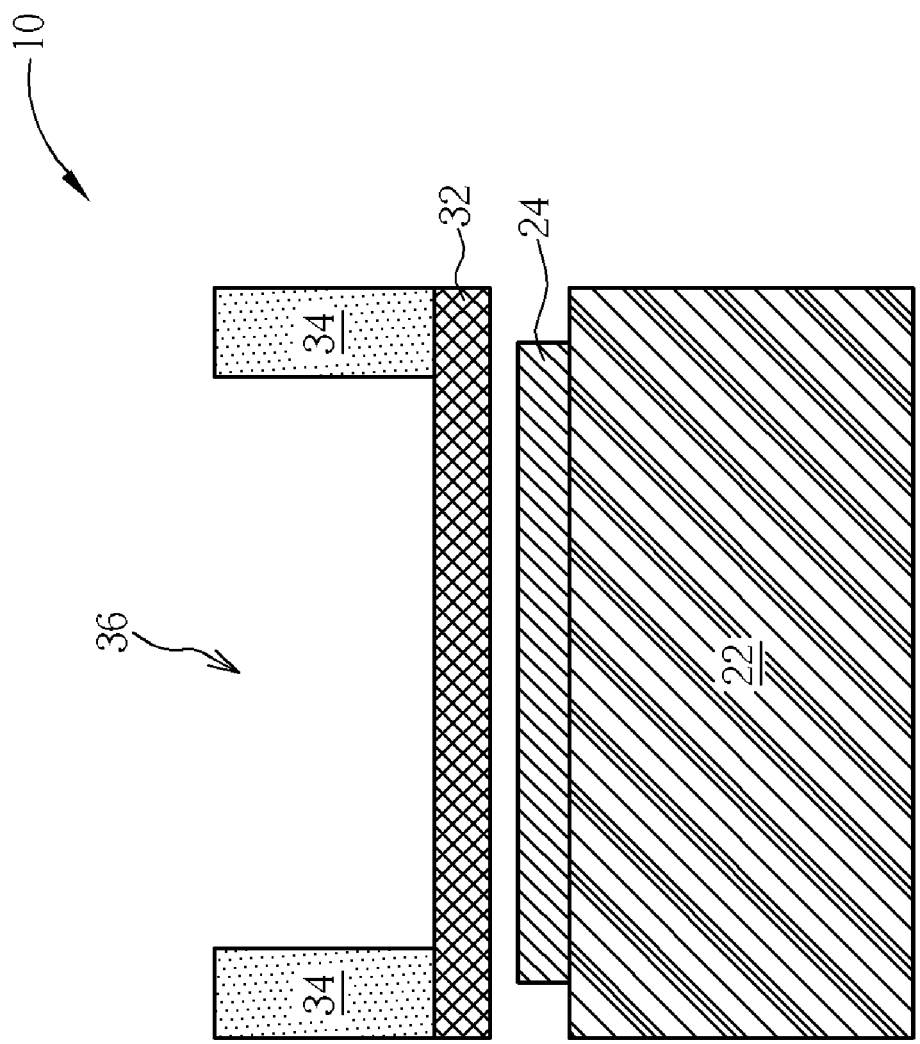
Figure 4:
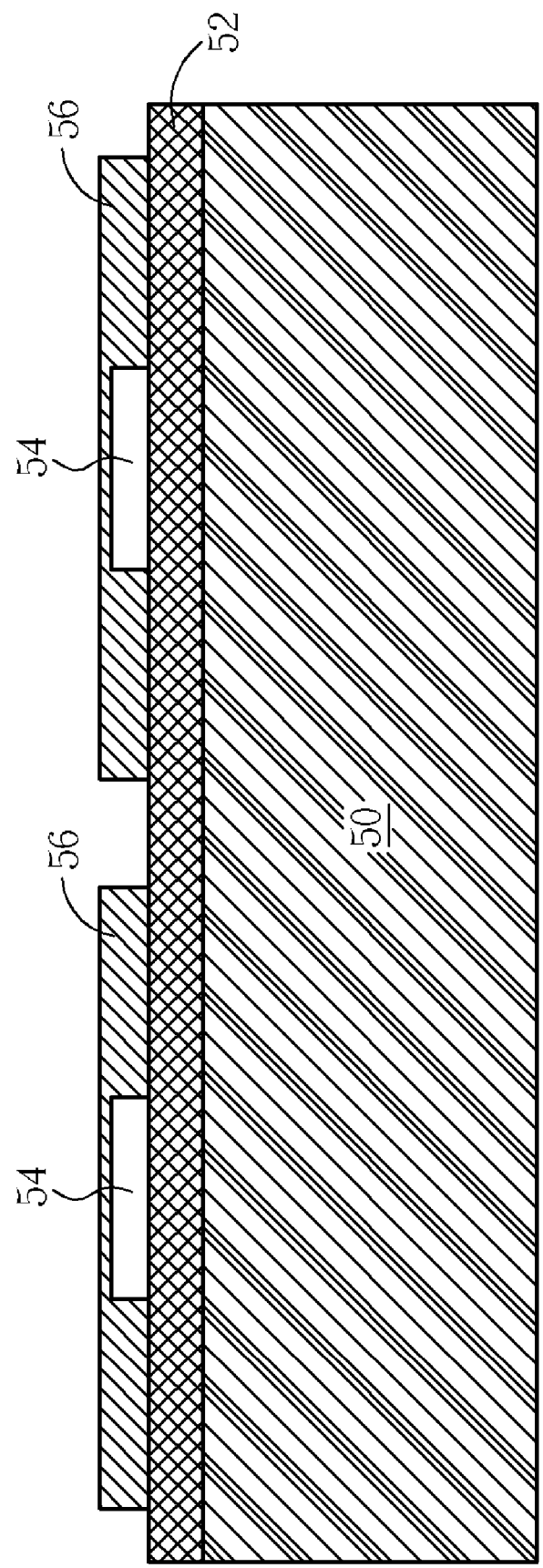
FIG. 4 through FIG. 7 are schematic diagrams illustrating a method of fabricating micro sample heating apparatuses according to a preferred embodiment of the present invention.

Please refer to FIG. 4 through FIG. 7. FIG. 4 through FIG. 7 are schematic diagrams illustrating a method of fabricating micro sample heating apparatuses according to a preferred embodiment of the present invention. As shown in FIG. 4, a substrate 50 is provided, and an insulating layer 52 is optionally formed on the first surface of the substrate 50. In this embodiment, the substrate 50 is an epitaxy substrate, but not limited to. The insulating layer 52 can be silicon oxide, silicon nitride, silicon oxynitride, or any suitable single-layer or multi-layer dielectric materials. Subsequently, a plurality of micro heating devices are formed on the insulating layer 52. In this embodiment, the step of forming the micro heating devices includes forming a metal layer 54 and a metal wiring layer 56 on the insulating layer 52. The metal layer 54, which serves as a heating layer, can be a platinum (Pt) layer formed by lift-off techniques, and the metal wiring layer 56 can be formed in the same manner. The metal layer 54 and the metal wiring layer 56 constitute the micro heating devices. It is appreciated that the materials of the metal layer 54 and the metal wiring layer 56 are not limited, and the metal layer 54 and the metal wiring layer 56 can be formed by other methods such as etching.

Figure 5:
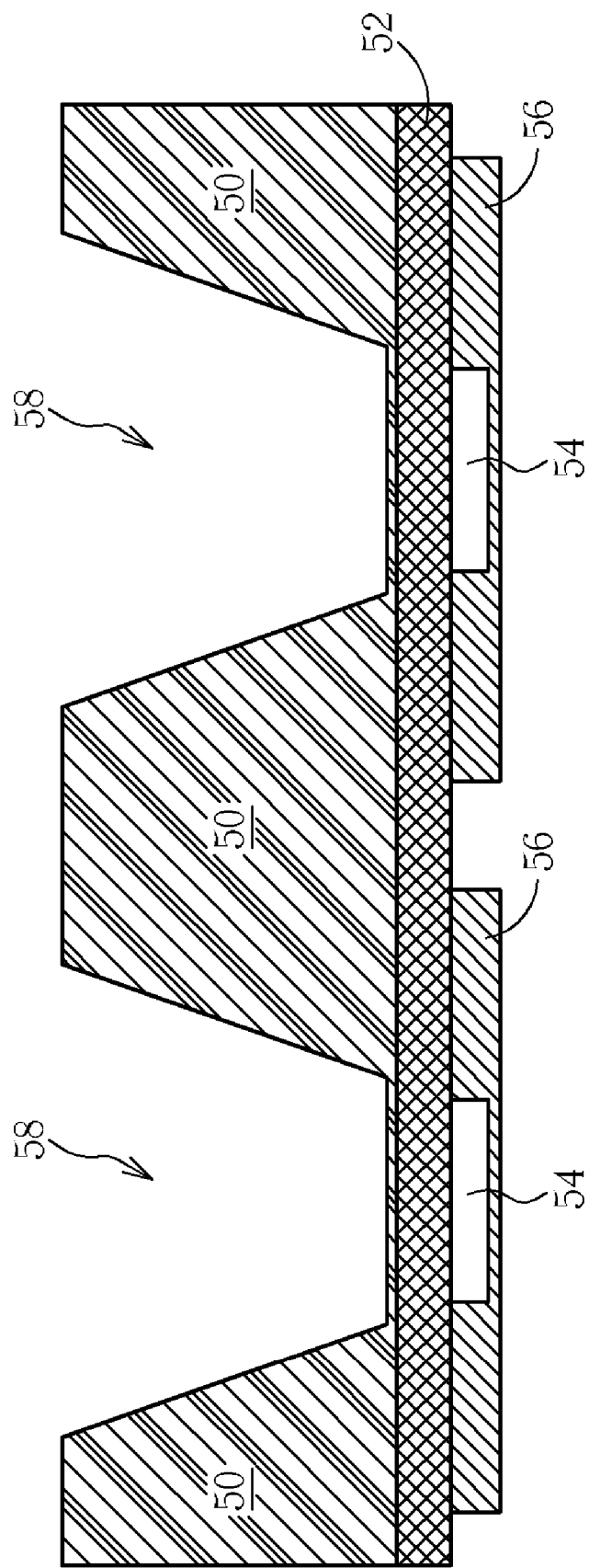

As shown in FIG. 5, the substrate 50 is turned over, and a plurality of cavities 58 corresponding to the micro heating devices are formed in the second surface of the substrate 50. Each cavity 58 has an inclined sidewall. In this embodiment, since the substrate 50 is an epitaxy substrate, the inclined sidewall of the cavities 58 can be formed by an anisotropic wet etching process e.g. an electro-chemical etching (ECE) process. It is also appreciated that the substrate 50 can be either etched through or not when forming the cavities 58. In this embodiment, the substrate 50 is not completely etched, so that the function of the substrate 50 and the insulating layer 52 positioned in the bottom of the cavities 58 is equivalent to a slide. The thickness of the insulating layer 52 can be calculated in advance, and the thickness of the substrate 50 positioned in the bottom of the cavities 58 can be controlled by etching end point detection techniques or by selecting the epitaxy substrates with different thickness. In addition, if the substrate 50 is etched through when forming the cavities 58, the thickness of the insulating layer 52 is equivalent to the thickness of the slide, and the insulating layer 52 also works as an etching stop in that case. The thickness of the substrate 50 positioned in the bottom of the cavities 58 is equivalent to the thickness of the slide if the insulating layer 52 is not formed.

Figure 6:
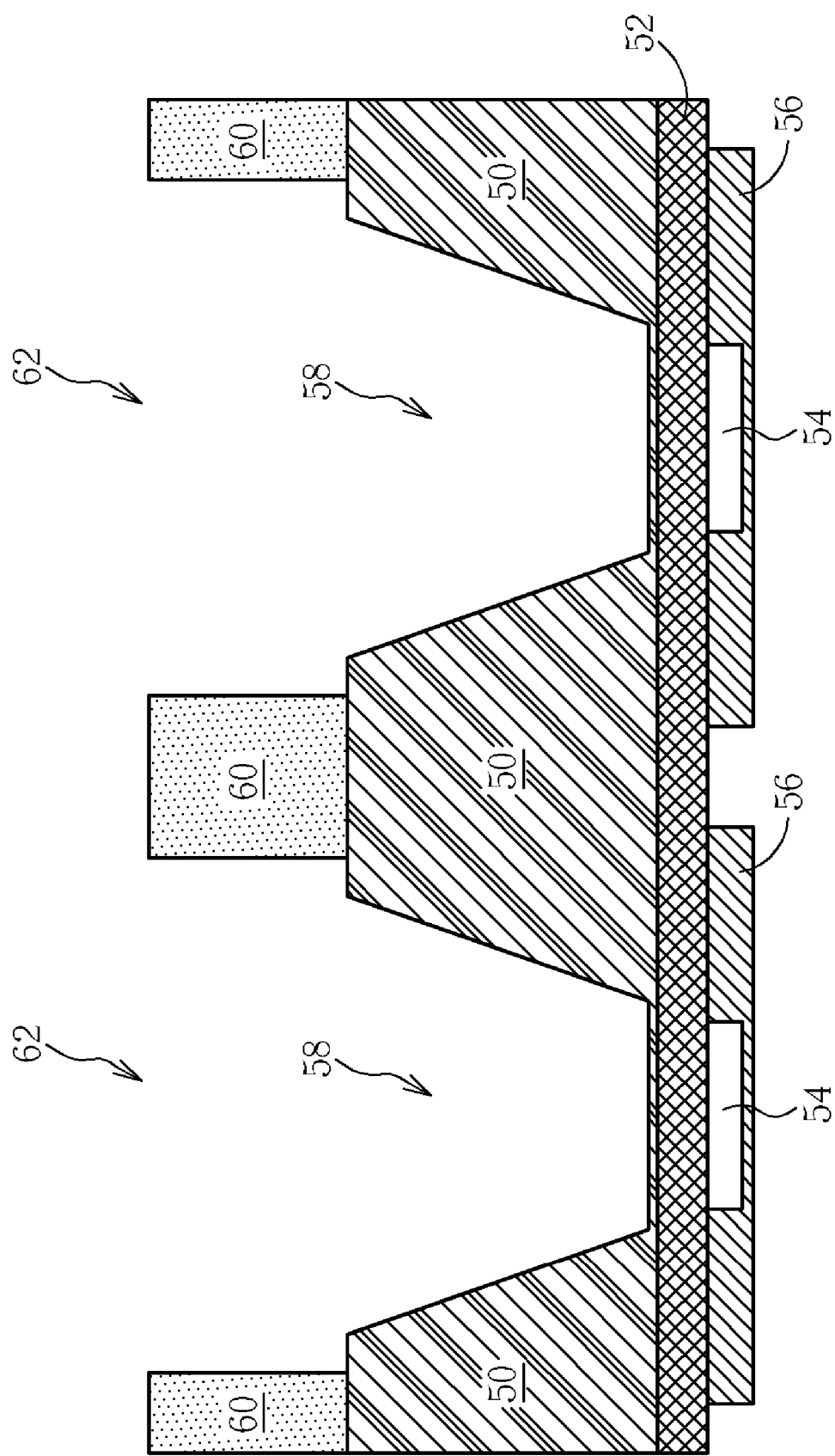

As shown in FIG. 6, an isolation structure 60 having a plurality of openings 62 is provided. The openings 62 are then aligned to the cavities 58 and the isolation structure 60 is bonded to the second surface of the substrate 50. Each cavity 58 and each opening 62 corresponding to the cavity 58 form a sample room. In this embodiment, the material of the isolation structure 60 is glass, and therefore the isolation structure 60 and the substrate 50 can be adhered together by anodic bonding techniques. However, if a different material is selected, other bonding techniques can be used.

Figure 7:
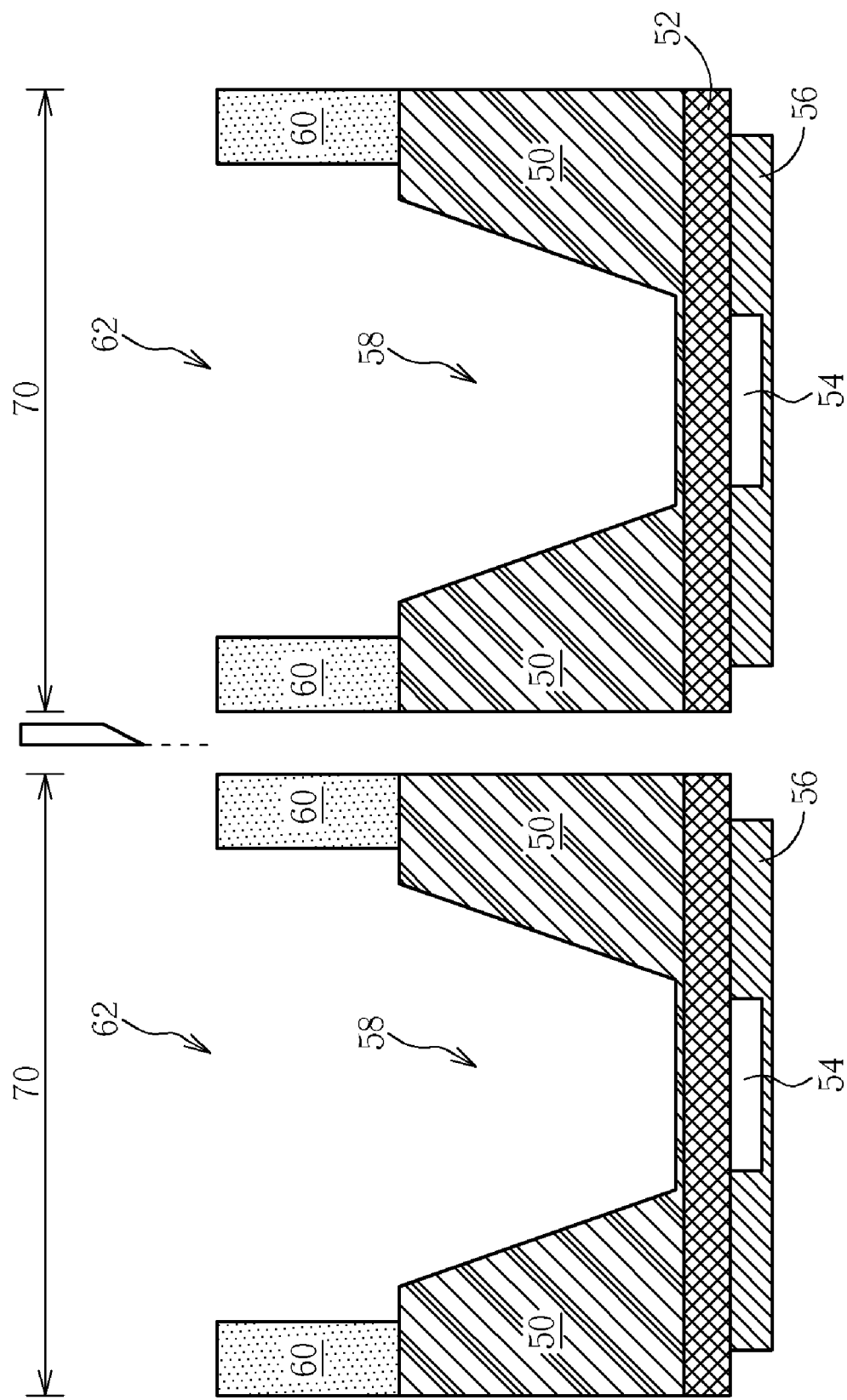

As shown in FIG. 7, a segment process is subsequently performed to divide the substrate 50 and the isolation structure 60 to form the micro sample heating apparatus 70.

In summary, the micro sample heating apparatus and method thereof of the present invention has the following advantages:

1) The method of the present invention is wafer level.

2) The method of the present invention is an integrated method that can improve heating efficiency and the micro sample heating apparatus does not have to be packaged individually.

3) The method of the present invention replaces the slide with a thin film (the substrate and the insulating layer), and therefore reduces heating time.

4) The method of the present invention does not need to assemble the heating unit and the sample room unit.

5) The method of the present invention can reduce the size of the micro sample heating apparatus.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A micro sample heating apparatus, comprising:
   a substrate;
   a micro heating device disposed on a first surface of the substrate;
   a cavity having an inclined sidewall and corresponding to the micro heating device positioned in a second surface of the substrate; and
   an isolation structure positioned on the second surface of the substrate, the isolation structure having an opening corresponding to the cavity;
   wherein the cavity and the opening form a sample room.

2. The micro sample heating apparatus of claim 1, wherein the substrate is an epitaxy substrate.

3. The micro sample heating apparatus of claim 1, further comprising an insulating layer disposed between the first surface of the substrate and the micro heating device.

4. The micro sample heating apparatus of claim 1, wherein the micro heating device comprises a metal layer disposed on the first surface of the substrate, and a metal wiring layer disposed on the metal layer.

5. The micro sample heating apparatus of claim 1, wherein the cavity does not penetrate through the substrate.

6. The micro sample heating apparatus of claim 1, wherein the isolation structure comprises glass.

7. A method of fabricating micro sample heating apparatuses, comprising:
   providing a substrate, and forming a plurality of micro heating devices on a first surface of the substrate;
   forming a plurality of cavities corresponding to the micro heating devices in a second surface of the substrate, each cavity having an inclined sidewall;
   providing an isolation structure having a plurality of openings; and
   bonding the isolation structure to the second surface of the substrate, each opening being corresponding to each cavity;
   wherein each cavity and each opening corresponding to the cavity form a sample room.

8. The method of claim 7, further comprising forming an insulating layer on the first surface of the substrate prior to forming the micro heating devices.

9. The method of claim 7, wherein forming the micro heating devices comprises:
   forming a metal layer on the first surface of the substrate; and
   forming a metal wiring layer on the metal layer.

10. The method of claim 9, wherein the metal layer and the metal wiring layer are formed by lift-off techniques.

11. The method of claim 7, wherein the substrate is an epitaxy substrate.

12. The method of claim 7, wherein the cavity is formed by an electro-chemical etching process.

13. The method of claim 12, wherein the electro-chemical etching process does not etch through the substrate.

14. The method of claim 7, wherein the isolation structure comprises glass.

15. The method of claim 7, wherein the isolation structure is bonded to the substrate by anodic bonding techniques.

16. The method of claim 7, further comprising performing a segment process to form a plurality of micro sample heating apparatuses subsequent to bonding the isolation structure to the substrate.

* * * * *